United States Patent
Welch (10) Patent No.: US 7,400,459 B2
(45) Date of Patent: Jul. 15, 2008

(54) OPERATING ROOM MAGNIFIER

(76) Inventor: Gracie L. Welch, 4311 Shirley Ave., Lynwood, CA (US) 90262

(*) Notice: Subject to any disclaimer, the term of this patent is extended or adjusted under 35 U.S.C. 154(b) by 0 days.

(21) Appl. No.: 11/119,843

(22) Filed: May 2, 2005

(65) Prior Publication Data
US 2005/0243441 A1 Nov. 3, 2005

Related U.S. Application Data

(60) Provisional application No. 60/567,373, filed on May 1, 2004.

(51) Int. Cl.
*G02B 27/02* (2006.01)

(52) U.S. Cl. .................. 359/802; 359/800; 362/455; 606/17

(58) Field of Classification Search ............ 359/802
See application file for complete search history.

(56) References Cited

U.S. PATENT DOCUMENTS

| 354,976 A | 12/1886 | Field ............ 248/484 |
|---|---|---|
| 3,510,204 A | 5/1970 | Jack ............ 350/244 |
| D229,231 S | 11/1973 | Beeren ............ D57/1 E |
| 3,945,717 A | 3/1976 | Ryder et al. ............ 350/237 |
| 4,190,322 A | 2/1980 | Wortley ............ 350/181 |
| 4,245,623 A * | 1/1981 | Erb ............ 128/831 |
| D264,598 S | 5/1982 | Matthews et al. ............ D16/135 |
| 4,626,971 A * | 12/1986 | Schultz ............ 362/154 |
| 4,744,019 A | 5/1988 | Krogsrud ............ 362/402 |
| 4,870,964 A | 10/1989 | Bailey, Jr. et al. ............ 128/303.1 |
| D323,132 S | 1/1992 | Grennan ............ D11/87 |
| 5,183,193 A | 2/1993 | Brandell ............ 224/219 |
| 5,396,366 A * | 3/1995 | Brown et al. ............ 359/435 |
| 5,495,286 A | 2/1996 | Adair ............ 348/68 |
| D374,020 S | 9/1996 | Dunn ............ D16/131 |
| D377,032 S | 12/1996 | Morooka ............ D16/202 |
| D392,760 S | 3/1998 | Wu ............ D26/62 |
| D403,338 S | 12/1998 | Dunn ............ D16/131 |
| 5,847,883 A | 12/1998 | Rispoli, Sr. ............ 359/802 |
| 6,086,228 A * | 7/2000 | McGowan et al. ............ 362/396 |
| 6,088,173 A | 7/2000 | Mendeksohn et al. ............ 359/802 |
| 6,322,226 B1 | 11/2001 | Dickson ............ 362/33 |
| D454,969 S | 3/2002 | Jacquelin ............ D26/51 |
| 6,384,988 B1 | 5/2002 | Muller et al. ............ 359/798 |
| 6,508,759 B1 * | 1/2003 | Taylor et al. ............ 600/168 |
| 2002/0101667 A1 | 8/2002 | Giampavolo et al. ............ 359/2 |

* cited by examiner

*Primary Examiner*—Jessica T Stultz
(74) *Attorney, Agent, or Firm*—Kenneth L. Green; Edgar W. Averill, Jr.

(57) ABSTRACT

An operating room magnifier is adapted to utilize an operating room light source and may be sterilized to allow use on a sterile field. The magnifier comprises a base, a neck, and a lens frame. The lens frame holds a lens and receives a light connected to the light source, providing a light beam to an object held under the magnifying glass. The light source may be a known fiber optics light source commonly used in operating rooms, or a special dedicated light source. The magnifier is particularly useful in identifying microsurgical instruments.

20 Claims, 8 Drawing Sheets

OPERATING ROOM MAGNIFIER

The present application claims the benefit of U.S. Provisional Application Ser. No. 60/567,373, filed May 1, 2004, which application is incorporated herein by reference.

BACKGROUND OF THE INVENTION

The present invention relates to magnifiers and in particular to a sterile magnifier for operating room use.

Modern surgery often involves reconstruction of very small and detailed structures. Such reconstruction procedures often require delicate manipulation of tissue and/or bone using very specialized and tools (e.g., microsurgical instruments) having very small working ends, which are difficult to distinguish with the naked eye. Surgical technicians and others are required to properly identify multiple specific microsurgical instruments used during each step of such procedures. The surgical technicians must be able to quickly and properly identify and handle these microsurgical tools throughout a procedure and failure to quickly and properly identify microsurgical tools may lengthen the procedure, make the surgeon's job more difficult, or degrade the results. Unfortunately, increasing the length of such procedures may be a detriment to a patient's recovery or even place the patient's life at risk, for example when internal bleeding must be stopped.

Some medical procedures, for example a cataract extraction or other ophthalmic surgery, are generally performed with lights turned off in an operating room. The only lights that remain on are the microscope lights that the surgeon is using to provide light to perform the procedure. In this instance, lights normally provided for viewing instruments are not available. As a result, instrument selection is hampered by the difficulty in distinguishing specific instruments. The low light level may also make selection of a medicine difficult.

BRIEF SUMMARY OF THE INVENTION

The present invention addresses the above and other needs by providing an operating room magnifier which is adapted to utilize a known operating room light source and may be sterilized to allow use on a sterile field. The magnifier comprises a base, a neck, and a lens frame. The lens frame holds a lens and receives a light at an end of the light source, providing a light beam to an object held under the magnifying glass. The light source may be a known fiber optics light source commonly used in operating rooms, or a special dedicated light source. The magnifier is particularly useful in identifying microsurgical instruments.

In accordance with one aspect of the invention, there is provided an operating room magnifier. The magnifier comprises a base for supporting the magnifier, a lens holder, and a neck for mechanically connecting the lens holder to the base. A lens is held by the lens holder and a light adapter resides in the lens holder and is adapted to hold a common operating room fiber optics light, and to direct a light beam from the light to an area under the lens to illuminate an object being viewed through the lens. The magnifier is suitable for sterilization using common operating room sterilization methods.

In accordance with another aspect of the invention, there is provided an operating room magnifier. The magnifier comprises a base for supporting the magnifier, a lens holder, and a neck for mechanically connecting the lens holder to the base. A lens is held by the lens holder. The lens holder is adapted to hold a light and to direct a light beam from the light to an area under the lens to illuminate an object being viewed through the lens. The magnifier is autoclave compatible for sterilization. Further, the lens is easily removable and replaceable for sterilization separate from the lens holder.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1:
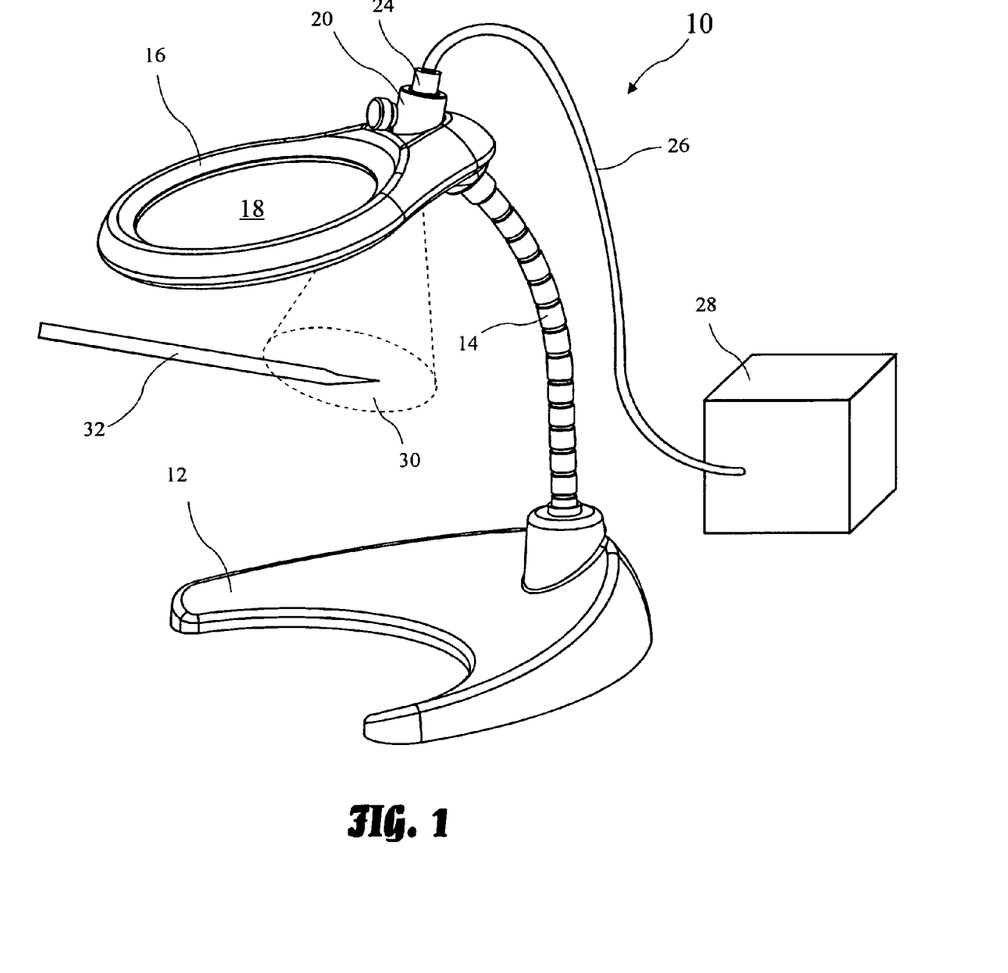
FIG. 1 is an operating room magnifier according to the present invention.

An operating room magnifier 10 according to the present invention is shown in FIG. 1. The magnifier 10 includes a base 12, a neck 14, and a lens holder 16. The neck 14 connects the lens holder 16 to the base 12. The lens holder 16 holds a lens 18 which allows magnification of an object 32, for example a microsurgical instrument, held under the lens 18.

Because some surgical procedures require a dark operating room, a light adapter 20 is provided to hold a light 24. The light adapter 20 is adapted to hold the light 24 and direct a light beam 30 from the light 24 to an area under the lens 18 to illuminate the object 32 being viewed through the lens 18. A preferred light 24 is provided by a fiber optics light source or a Light Emitting Diode (LED) light source. A more preferred light is provided by a fiber optics light source, and a most preferred light is provided by a common operating room fiber optics light source. An example of a common operating room fiber optics light source is an Light Source made by Medovations Inc. In Milwaukee, Wis. The light 24 is connected by, for example, a fiber optics cable 26 to a light source 28. While the magnifier is described herein with a fiber optics light source, the present invention is intended to encompass magnifiers with any light suitable for use in an operating room.

The lens 18 is preferably approximately four inches in diameter and the neck 14 is preferably approximately eight inches long. The lens holder 16 and the base 12 are preferably made from metal and more preferably from aluminum, and preferably have a polished finish. The base 12 is preferably made from a solid material with sufficient weight to stably support the neck 14 and lens holder 16. The neck 14 is preferably made from stainless steel flex. The magnifier 10 is suitable for sterilization using common operating room sterilization methods, and the magnifier 10 is preferably autoclave compatible for sterilization.

A magnifier according to the present invention may also be used in a home or office. In such uses, an LED light source may be preferred. An example of an LED light source is a Miniature LED Illuminator made by Stockeryale, Inc. in Salem, N.H. Because sterilization will not be required in the home or office, the magnifier may be constructed from materials used commonly in the home or office. For example, the neck 14 may be constructed from aluminum. The home or office magnifier may have a finish comprising chrome plating, brass plating, copper plating, enamel, baked enamel, E-coat, or vinyl clad.

Figure 2A:
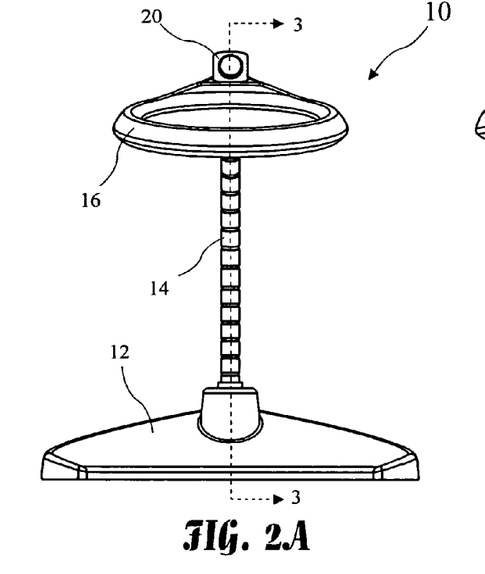
FIG. 2A is a front view of the magnifier.
Figure 2B:
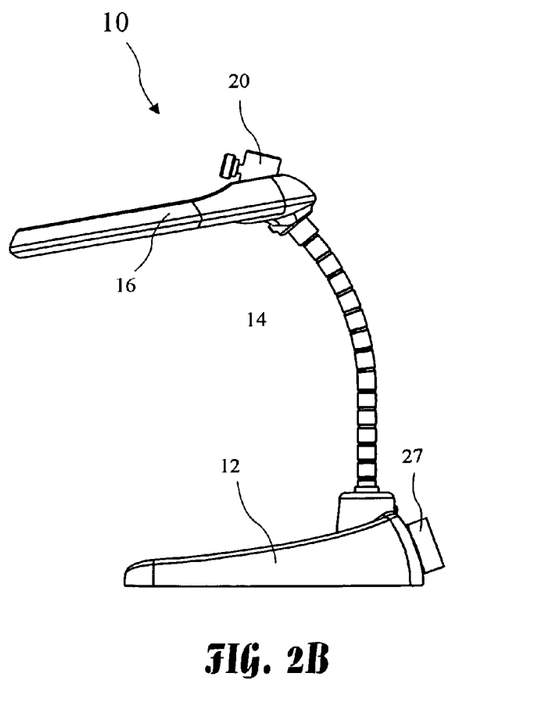
FIG. 2B is a side view of the magnifier.
Figure 2C:
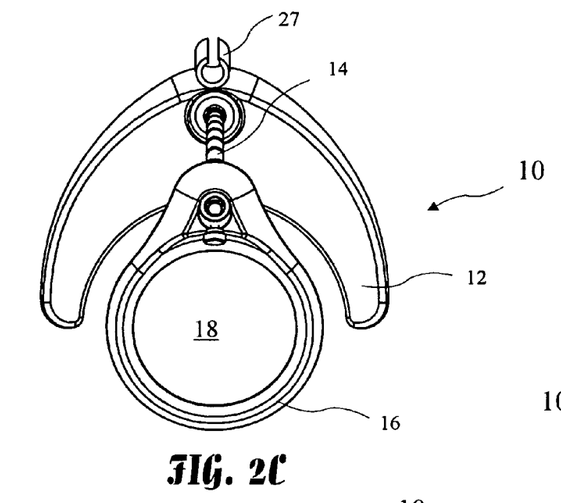
FIG. 2C is a top view of the magnifier.

A front view of the magnifier 10 is shown in FIG. 2A, a side view of the magnifier 10 is shown in FIG. 2B, and a top view of the magnifier 10 is shown in FIG. 2C. A cable holder 27 is attached to the 12 to allow the fiber optics cable 26 (see FIG. 1) to be held securely.

Figures 3, 3A:
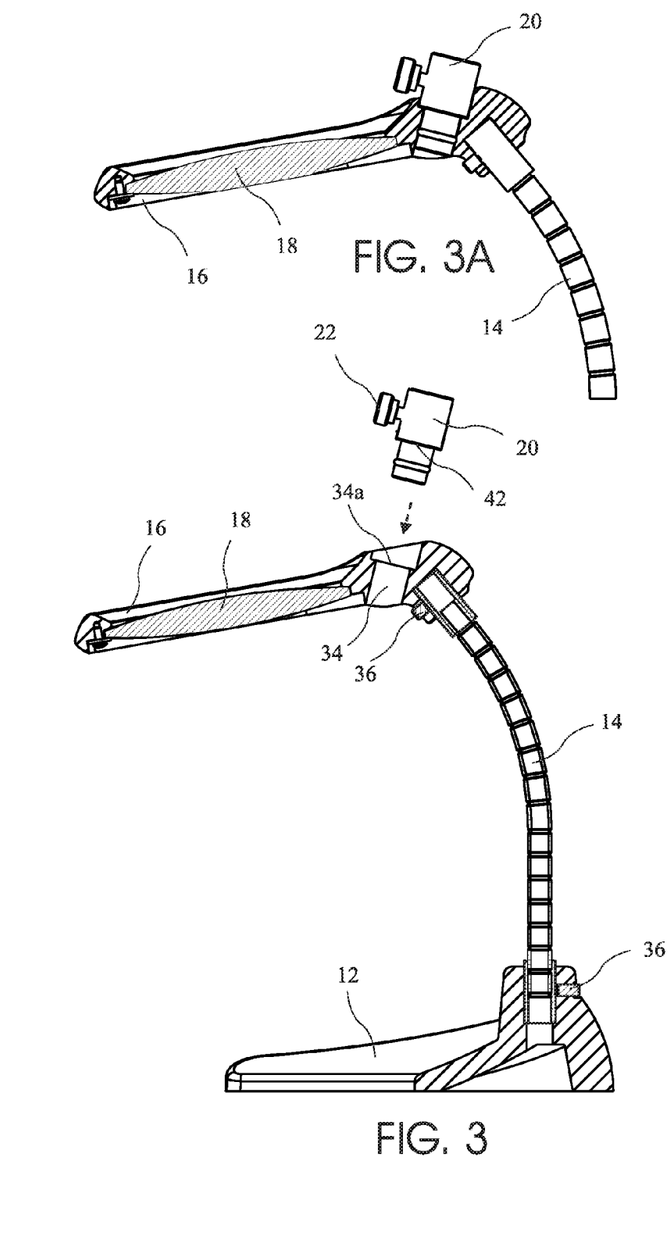
FIG. 3 is a cross-sectional view of the magnifier taken along line 3-3 of FIG. 2A with a light adapter removed from a lens holder.
FIG. 3A is a partial cross-sectional view of the magnifier taken along line 3-3 of FIG. 2A with the light adapter residing in the lens holder.

A cross-sectional view of the magnifier 10 taken along line 3-3 of FIG. 2A with the light adapter 20 removed from the lens holder 16 is shown in FIG. 3 and a partial cross-sectional view of the magnifier 10 taken along line 3-3 of FIG. 2A with the light adapter 20 residing in the lens holder 16 is shown in FIG. 3A. The light adapter 20 includes a thumbscrew 22 which may be used to hold a light 24 (see FIG. 1) in place to direct a light beam 30 from the light 24 to an area under the lens 18 to illuminate an object 32 being viewed through the lens 18. The mouth 34 includes a mouth step 34a and the adapter 20 includes an adapter step 42. The adapter step 42 is seen seated against the mouth step in FIG. 3A.

Figure 3B:
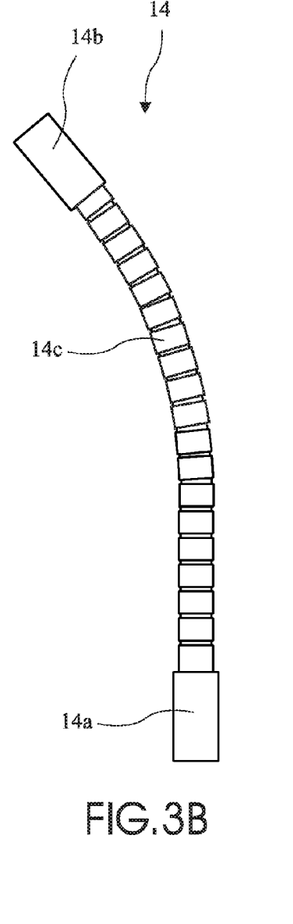
FIG. 3B shows end portions of the neck.

A first end portion 14a of the neck 14 is removably insertable into a first neck receptacle 44a (see FIG. 16) in the base 12, and a second end portion of the neck 14 is insertable into a second neck receptacle 44b (see FIG. 13) in the lens holder 16, wherein set screws 36 intersect the receptacles 44a and 44b to hold the end portions 14a and 14b of the neck 14 in place in the receptacles 44a and 44b. The neck 14 end portions 14a and 14b are shown in FIG. 3B. The end portions 14a and 14b are preferably approximately 0.5 inches in diameter and approximately one inch long. A neck center portion 14c is preferably approximately 0.38 inches in diameter.

Figures 4, 5A, 5B:
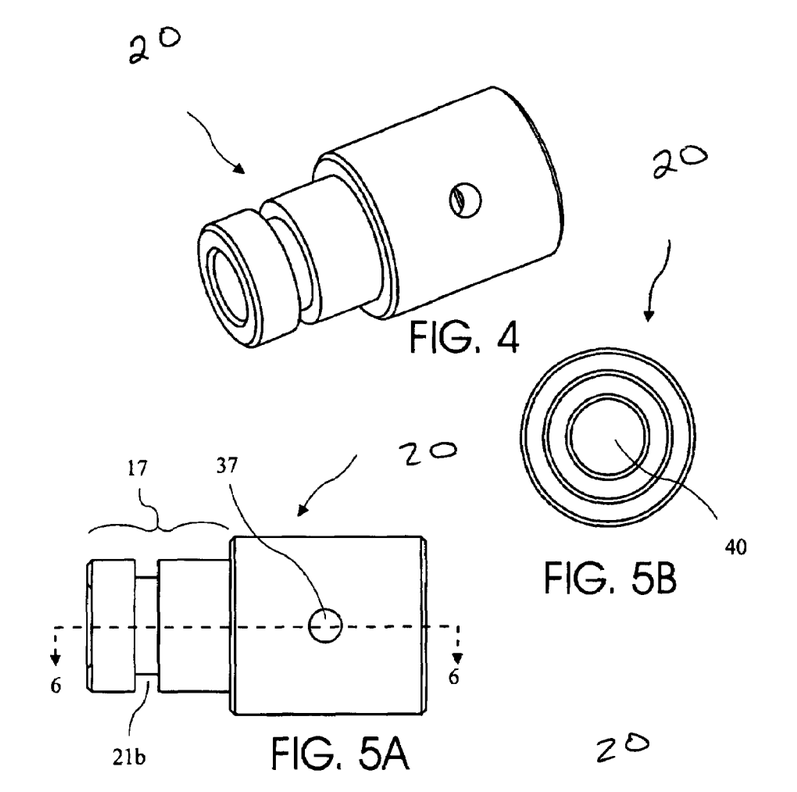
FIG. 4 is a perspective view of the light adapter.
FIG. 5A is a side view of the light adapter.
FIG. 5B is an end view of the light adapter.
Figures 6, 7:
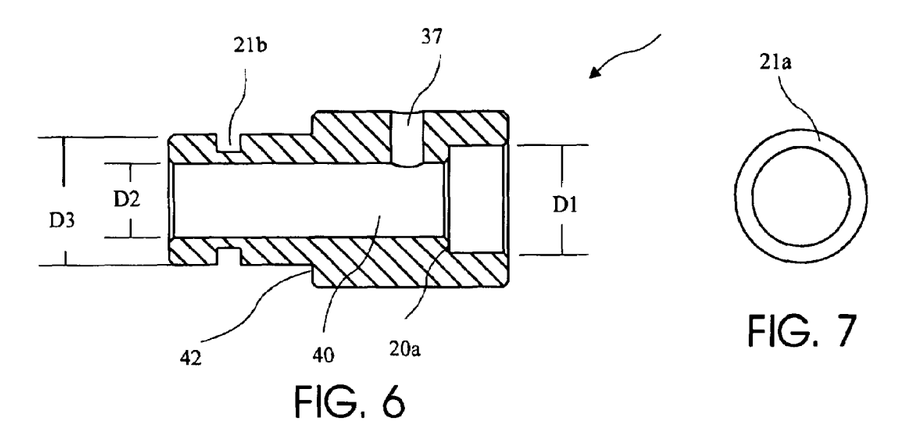
FIG. 6 is a cross-sectional view of the light adapter taken along line 6-6 of FIG. 5A.
FIG. 7 is an o-ring adapted to reside in an o-ring groove on the light adapter.

A perspective view of the light adapter 20 is shown in FIG. 4, a side view of the light adapter 20 is shown in FIG. 5, and an end view of the light adapter 20 is shown in FIG. 5A. A cross-sectional view of the light adapter 20 along line 6-6 of FIG. 5A is shown in FIG. 6. The light adapter 20 includes a threaded thumbscrew passage 37 to allow the thumbscrew 22 (see FIG. 3) to be advanced against the light 24 to hold the light 24 in the light adapter 20. The light adapter 20 further includes a shoulder 42 to position the light 24 in the light adapter 20, and an o-ring groove 21b for seating an o-ring 21a (see FIG. 6A) on the light adapter 20. For use with one common size light 24, a greater inner diameter D1 of the light adapter 20 is preferably approximately 0.45 inches and a lesser inner diameter D2 of the light adapter 20 is preferably approximately 0.31 inches. For use with another common size light, the lesser inner diameter D2 of a mouth 40 of the light adapter 20 is preferably approximately 2 mm or less. The light adapter 20 is thus sized to accept a common operating room fiber optics light. The light adapter 20 includes a stepped down portion 17 for insertion into the adapter mouth 23 (see FIG. 3) having an outside diameter D3 of preferably approximately 0.543 inches and is preferably approximately 0.6 inches long and includes o-ring groove 21b.

The o-ring 21a is shown in FIG. 7. The o-ring 21a provides an interference fit between the light adapter 20 and the adapter mouth 34 to hold the light adapter 20 in the adapter mouth 34.

Figure 8:
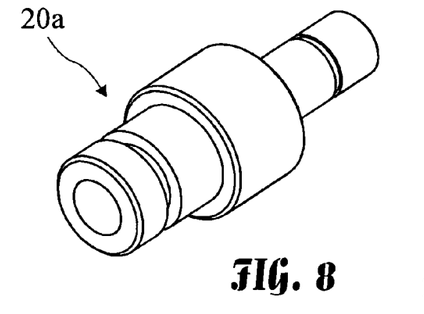
FIG. 8 is a perspective view of a universal light adapter.
Figure 9A:
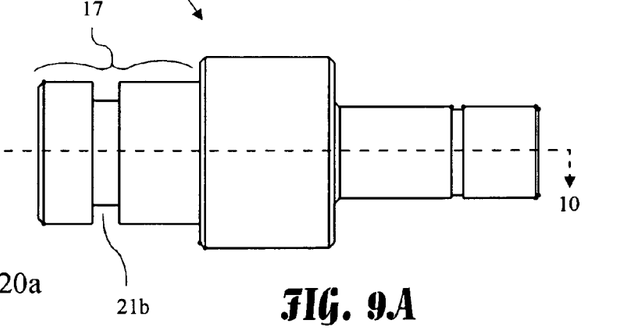
FIG. 9A is a side view of the universal light adapter.
Figure 9B:
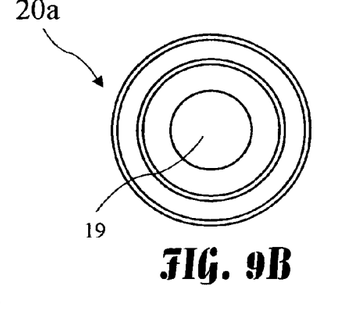
FIG. 9B is an end view of the universal light adapter.
Figure 10:
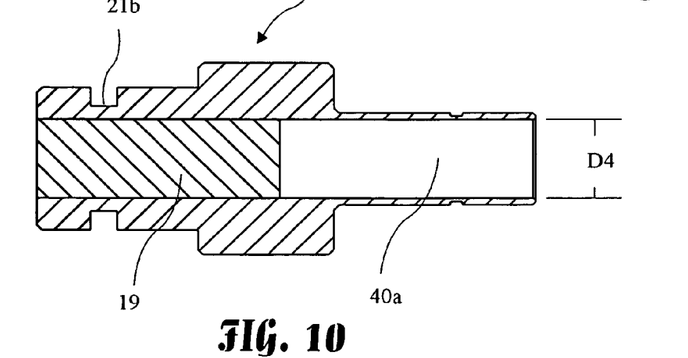
FIG. 10 is a cross-sectional view of the universal light adapter taken along line 10-10 of FIG. 9A.

A perspective view of a universal adapter 20a is shown in FIG. 8, a side view of the universal adapter 20a is shown in FIG. 9A, and an end view of the universal adapter 20a is shown in FIG. 9B. The universal adapter 20a is suitable for adapting a variety of lights 24 associated with light sources commonly found in an operating room and includes the stepped down portion 17 with the o-ring groove 21b for holding the universal adapter 20a in the adapter mouth 34 (see FIG. 3). A second light receptacle 40a is preferably approximately 0.3 inches in diameter. A cross-sectional view of the universal adapter 20a taken along line 10-10 of FIG. 9A is shown in FIG. 10. An optical diffuser 19 resides inside the universal adapter 20a to provide the light beam 30 (see FIG. 1) from the light 24. The diffuser 19 is preferably approximately 0.9 inches long, is preferably approximately 0.3 inches in diameter (i.e., approximately the same diameter as the light receptacle 40a), and is preferably made from glass or acrylic.

Figures 11, 12:
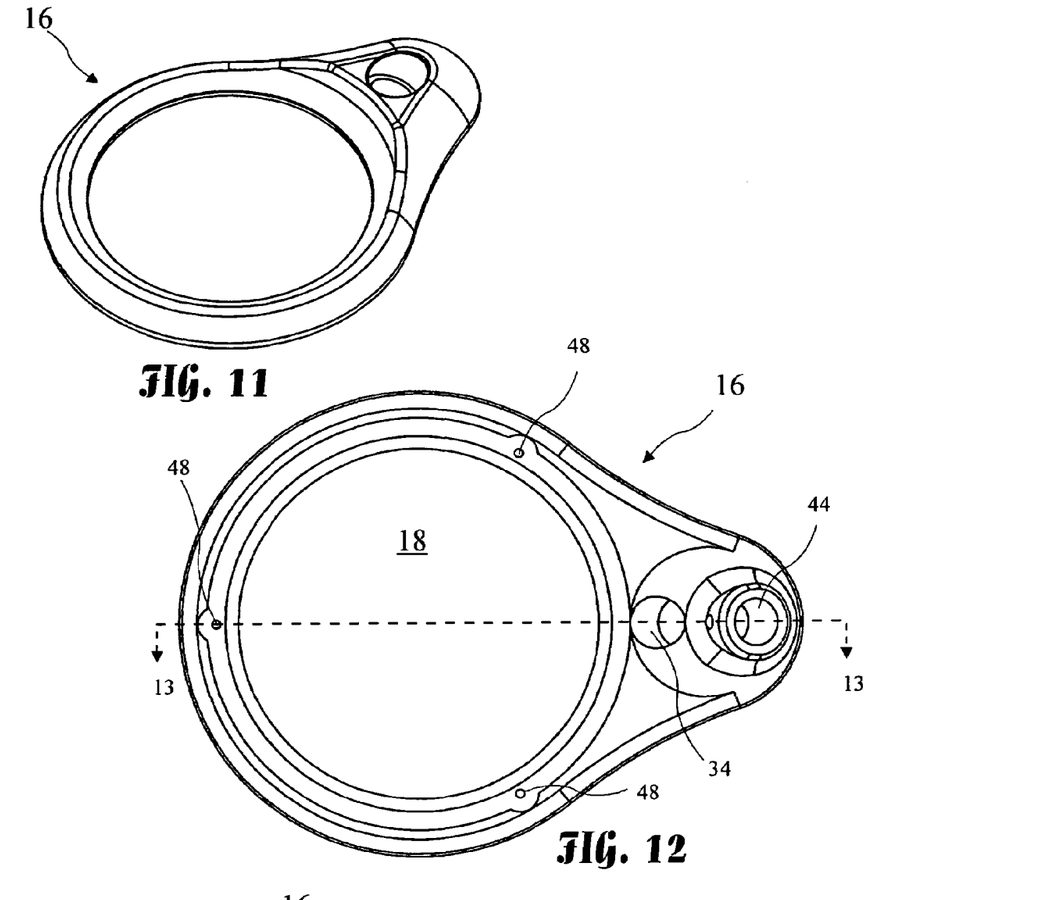
FIG. 11 is a perspective view of a lens holder of the magnifier.
FIG. 12 is a bottom view of the lens holder of the magnifier.
Figure 13:
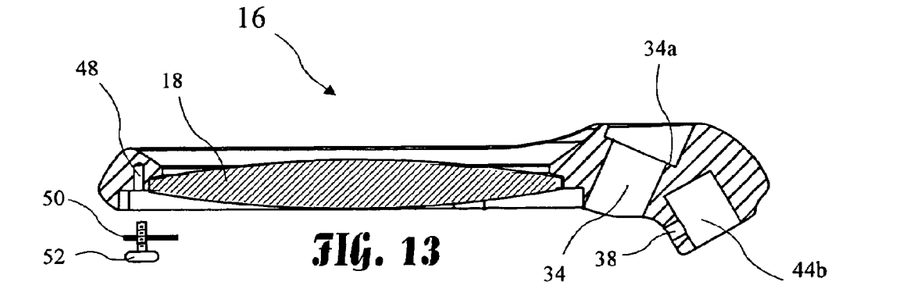
FIG. 13 is a cross-sectional view of the lens holder taken along line 13-13 of FIG. 12.

A perspective view of a bottom surface of the lens holder 16 is shown in FIG. 11, a bottom view of the lens holder 16 is shown in FIG. 12, and a cross-sectional view of the lens holder 16 taken along line 13-13 of FIG. 12 is shown in FIG. 13. The lens 18 is preferably held in the lens holder 16 using a three point mount preferably comprising threaded holes 48, lens washers 50, and lens screws 52, allowing easy removal and replacement of the lens 18 for sterilization or for selection of a lens 18 with a magnification preferred by a nurse or surgical technician. While a three point mounting system has been described here, the lens may be attached to the lens holder in any appropriate manner allowing removal and replacement. A threaded set screw passage 38 approximately perpendicular to the neck receptacle 44b to allow a set screw to be advanced against the second neck end portion 14b.

A preferred lens is preferably adapted to be sterilized using an Ethylene Oxide gas sterilizer, such as the AN74i/Anprolen made by Andersen Products in Haw River, N.C. The lens holder 16, neck 14, and base 12 may also be sterilized using an Ethylene Oxide gas sterilizer, or by other suitable sterilizers, for example, a steam sterilizer. The lens holder 16 includes an adapter mouth 34 includes a mouth shoulder 34a to position the light adapter 20 in the lens holder 16.

While a preferred embodiment of the magnifier 10 includes a light 24 mounted to the lens holder 16, the light 24 may be mounted to the magnifier 10 in any manner which provides a light beam 30 on an object 32 positioned for viewing under the lens 18. Any magnifier adapted for sterilization and including a mounting or adapter for thus holding a light is intended to come within the scope of the present invention.

Figure 14:
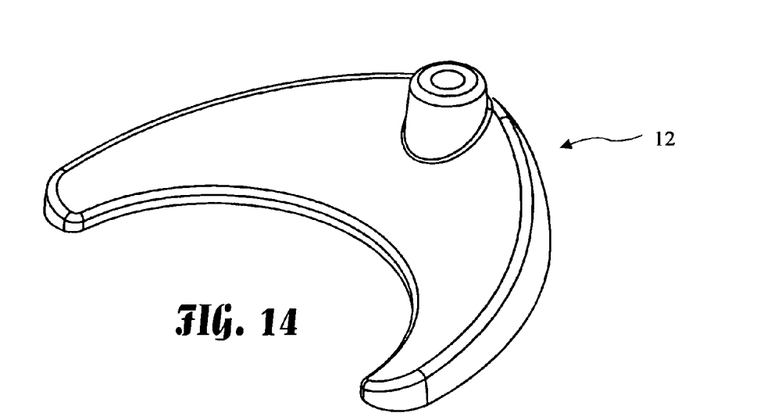
FIG. 14 is a perspective view of a base of the magnifier.
Figures 15, 16:
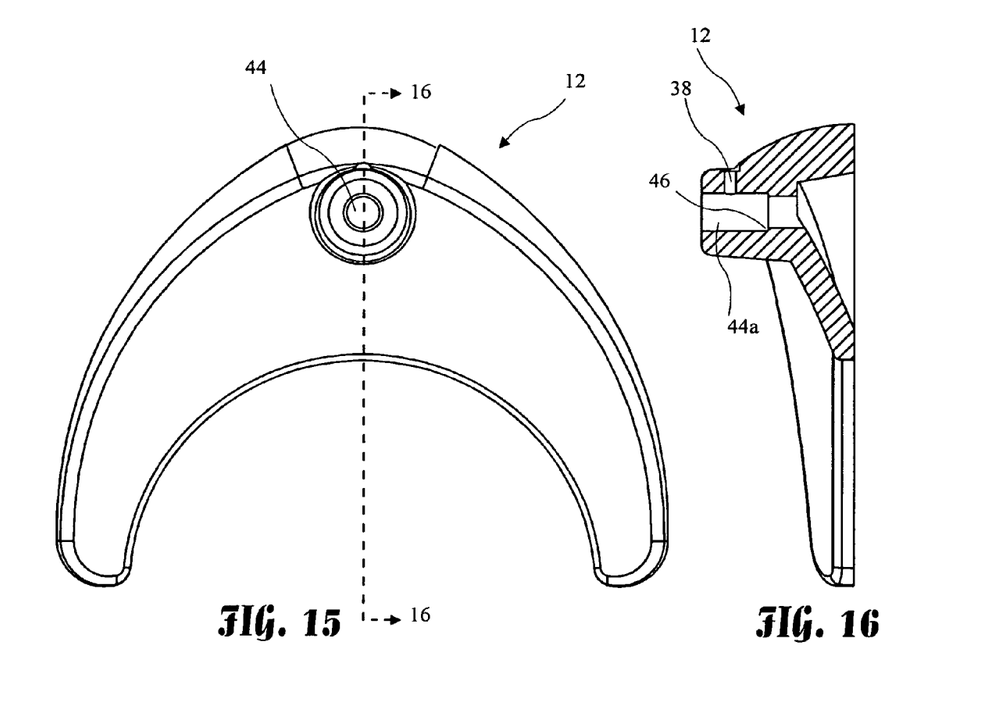
FIG. 15 is a top view of the base.
FIG. 16 is a cross-sectional view of the base taken along line 16-16 of FIG. 15.

A perspective view of the base 12 is shown in FIG. 14, a top view of the base 12 is shown in FIG. 15, and a cross-sectional view of the base 12 taken along line 16-16 of FIG. 15 is shown in FIG. 16. The neck receptacle 44a includes a receptacle shoulder 46 to position the neck 14 within the neck receptacle 44b, and a threaded set screw passage 38 approximately perpendicular to the neck receptacle 44a to allow a set screw to be advanced against the first neck end portion 14a.

Figure 17:
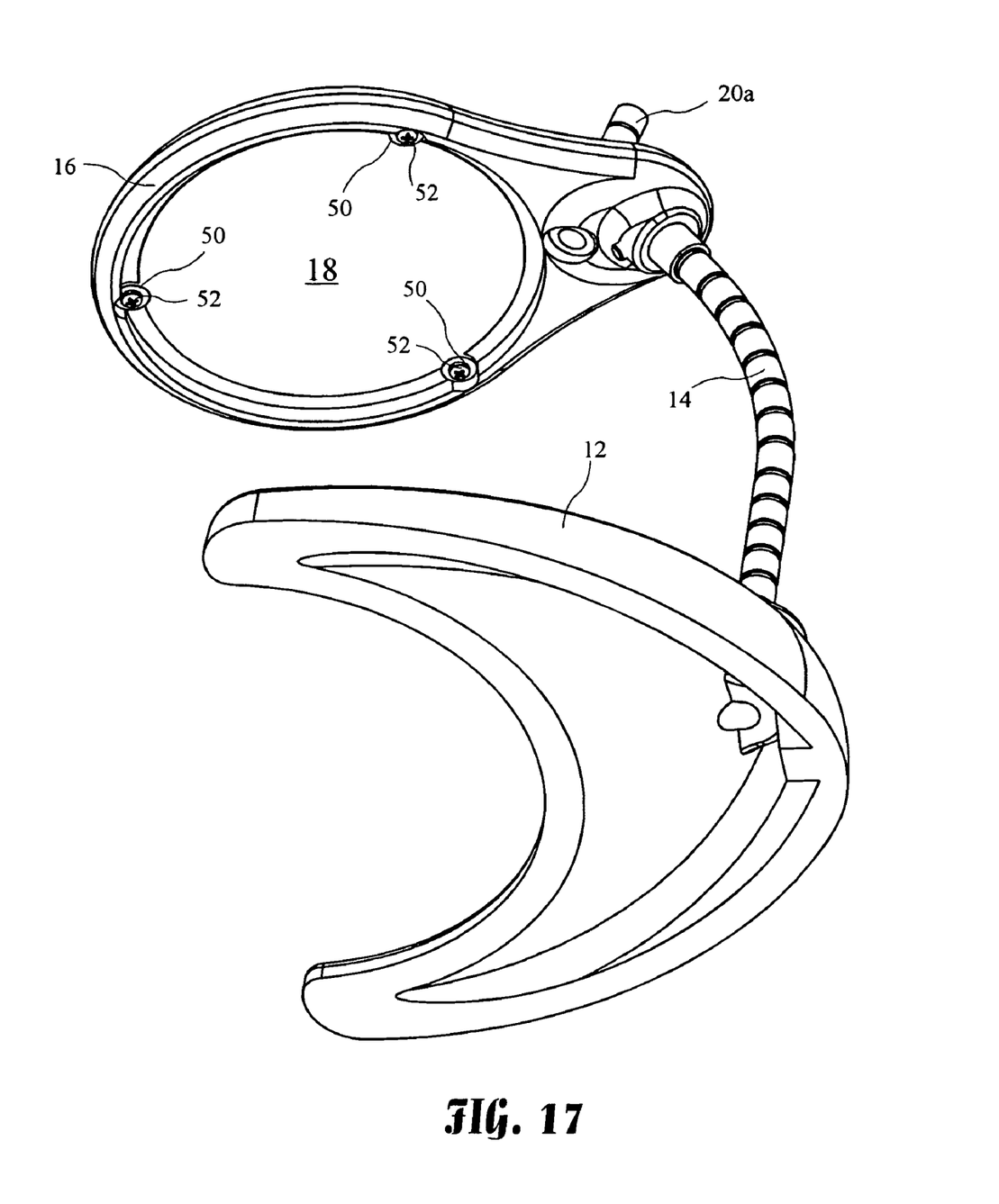
FIG. 17 is a bottom perspective view of the magnifier.

A bottom perspective view of the magnifier 10 is shown in FIG. 17. The lens washers 50 and lens screws 52 are shown holding the lens 18 in the lens holder 16. The universal adapter 20a is shown residing in the adapter mouth 34 (see FIG. 13).

While the invention herein disclosed has been described by means of specific embodiments and applications thereof, numerous modifications and variations could be made thereto by those skilled in the art without departing from the scope of the invention set forth in the claims.

I claim:

1. An operating room magnifier comprising:
   a base for supporting the magnifier;
   a lens holder;
   a lens held by the lens holder;
   a neck for mechanically connecting the lens holder to the base;
   an operating room light;
   a cylindrical light adapter including a mouth configured to accept the operating room light;
   a cylindrical adapter mouth opening upward in the lens holder configured to accept the light adapter, and
   an o-ring residing on the exterior of the light adapter to provide an interference fit between the light adapter and the adapter mouth to hold the light adapter in the adapter mouth,
   wherein the magnifier is suitable for sterilization using common operating room sterilization methods.

2. The magnifier of claim 1, wherein the magnifier is autoclave compatible.

3. The magnifier of claim 1, wherein the lens is removable and replaceable from the lens holder to allow separate sterilization of the lens.

4. The magnifier of claim 1, wherein the light adapter is adapted to direct the light beam toward an area under the lens to illuminate an object being viewed through the lens.

5. The magnifier of claim 1, wherein the light adapter is adapted to receive a fiber optics light.

6. The magnifier of claim 5, wherein the light adapter is adapted to receive a common operating room fiber optics light.

7. The magnifier of claim 1, wherein the light adapter is adapted to receive a Light Emitting Diode (LED) light.

8. The magnifier of claim 1, wherein the light adapter includes an adapter step and a stepped down region and the mouth includes a mouth step, and wherein the mouth step and the adapter step cooperate to seat the light adapter in the adapter mouth.

9. The magnifier of claim 1, wherein the light adapter is a universal adapter for known operating room fiber optics lights.

10. The magnifier of claim 1, wherein the neck is an adjustable neck allowing the lens holder to be adjusted vertically or horizontally for better viewing.

11. The magnifier of claim 1, wherein a first end portion of the neck is removably insertable into a first neck receptacle in the base.

12. The magnifier of claim 1, wherein a second end portion of the neck is removably insertable into a second neck receptacle in the lens holder.

13. The magnifier of claim 1, wherein a first end portion of the neck is removably insertable into a first neck receptacle in the base, and a second end portion of the neck is insertable into a second neck receptacle in the lens holder, wherein set screws intersect the first and second receptacles to hold the end portions of the neck in place in the receptacles.

14. An operating room magnifier comprising:
   a base for supporting the magnifier;
   a lens holder;
   a lens held by the lens holder;
   a cylindrical adapter mouth including a mouth step, the adapter mouth opening upward in the lens holder;
   a cylindrical light adapter residing in the adapter mouth and adapted to hold an operating room light and direct a light beam from the light to an area under the lens to illuminate an object being viewed through the lens; and
   a neck for mechanically connecting the lens holder to the base,
   wherein the light adapter includes an adapter step and a stepped down region, wherein the mouth step and the adapter step cooperate to seat the light adapter in the adapter mouth, and wherein the magnifier is autoclave compatible.

15. The magnifier of claim 14, wherein the lens is removable and replaceable from the lens holder to allow separate sterilization of the lens.

16. The magnifier of claim 14, wherein the light adapter is adapted to receive a common operating room fiber optics light.

17. An operating room magnifier comprising:
   a base for supporting the magnifier;
   a lens holder;
   a lens held by the lens holder;
   an adapter mouth in the lens holder, the adapter mouth including an interior mouth step;
   light adapter residing in the adapter mouth and adapted to hold a common operating room fiber optics light and direct a light beam from the light to an area under the lens to illuminate an object being viewed through the lens;
   an adapter step and a cylindrical stepped down region of the light adapter for insertion into the adapter mouth, wherein the mouth step and the adapter step cooperate to seat the light adapter in the adapter mouth;
   an o-ring groove in the stepped down region of the light adapter;
   an o-ring residing in the o-ring groove of the light adapter to provide an interference fit between the stepped down region of the light adapter and the adapter mouth to hold the light adapter in the adapter mouth, and
   a neck for mechanically connecting the lens holder to the base,
   wherein the magnifier is suitable for sterilization using common operating room sterilization methods.

18. The magnifier of claim 17, wherein the magnifier is autoclave compatible.

19. The magnifier of claim 17, wherein the lens is removable and replaceable from the lens holder to allow separate sterilization of the lens.

20. The magnifier of claim 17, wherein the adapter mouth opens upward to accept the light adapter.

* * * * *